United States Patent [19]

Föll et al.

[11] 4,288,428

[45] Sep. 8, 1981

[54] UDDER DISINFECTANT AND METHOD OF DISINFECTING TEATS

[75] Inventors: Ake L. Föll, Södertälje; Stig G. Widell, Ödeshög, both of Sweden

[73] Assignee: Ewos Aktiebolaget, Södertälje, Sweden

[21] Appl. No.: 134,425

[22] Filed: Mar. 27, 1980

[30] Foreign Application Priority Data

Apr. 2, 1979 [SE] Sweden .............................. 7902893

[51] Int. Cl.³ ..................... A61K 31/74; A61K 31/18
[52] U.S. Cl. ...................................... 424/78; 424/80; 424/150
[58] Field of Search .................. 424/150, 341, 78, 80

[56] References Cited

U.S. PATENT DOCUMENTS

| | | | |
|---|---|---|---|
| 2,931,777 | 4/1960 | Shelanski et al. | 424/150 |
| 4,017,407 | 4/1977 | Cantor et al. | 424/150 |
| 4,113,857 | 9/1978 | Shetty | 424/150 |

FOREIGN PATENT DOCUMENTS 1315461 5/1973 United Kingdom .

Primary Examiner—Sam Rosen
Attorney, Agent, or Firm—Brumbaugh, Graves, Donohue & Raymond

[57] ABSTRACT

Iodophorous udder disinfecting preparation comprising a iodophor in the form of an alkylphenoxypoly(ethyleneoxy)-ethanol-idodine complex or a polyvinylpyrrolidone-iodine complex, whereby the complex is present in an amount corresponding to 0.01, preferably 0.1 to 0.4%, by weight of free iodine, and 5 to 10% by weight of urea, an organic and/or inorganic acid to pH 1 to 5, and water and/or other solvent to 100% by weight, and whereby the udder disinfecting preparation according to a preferred embodiment further contains an alkoxylated glucose derivative in an amount of up to 4% by weight. By means of the udder disinfecting preparation a good bactericidal effect is obtained with a low iodine concentration, as well as a good skin emollient effect. The invention further relates to a method of increasing milk production by treating the teats with such an udder disinfectant.

17 Claims, No Drawings

UDDER DISINFECTANT AND METHOD OF DISINFECTING TEATS

TECHNICAL FIELD

The present invention relates to an udder disinfecting preparation comprising a iodophor in the form of an alkylphenoxypoly(ethyleneoxy)ethanol-iodine complex or a polyvinylpyrrolidone-iodine complex.

An object of the present invention is to obtain a iodophorous udder disinfecting preparation which does not cause teat chaps even at repeated daily use on the teats of milkcows, and comprising a complex of iodine with a nonionic surface active agent, and thereby having an improved skin emollient and bactericidal effect.

BACKGROUND OF THE INVENTION

Iodophors in which a part of or the whole amount of elementary iodine is in complex form with a nonionic surface active agent are commonly used in disinfecting preparations within the dairy industry. They are especially used for dipping the teats into after milking has taken place in order to prevent the formation of mastitis.

There are previously known udder disinfecting preparations comprising a iodophor in the form of a complex between iodine and nonionic surface active agents, as a complex between iodine and alkylphenoxypoly(ethyleneoxy)ethanol, and iodine and alkoxylated lanoline, whereby the latter has a skin moistening effect as well, by the effect of the lanoline. Above complexes are described in Swedish patent specification Nos. 145,966 and 357,886.

A continuous use of iodophorous disinfecting preparations without skin emollient features has resulted in a high frequency of chap formation in the teats. The chaps or fissures in the cutaneous tissue of the cow's teats will act as reservoirs for bacteria and it is difficult to penetrate these reservoirs with any type of aqueous disinfecting preparations. It is supposed that the dermatological changes causing chaps depend on the removal of the natural protecting fats of the skin by an emulgating process.

Although iodophorous preparations have a high bactericidal activity a number of them show the drawback that large amounts of ethoxylated surface active agents are needed to give a complete dissolution of their contents of elementary iodine. It is known that only about 20% of the iodine added are chemically bound to the surface active agent, the residue being titratable with standard solutions of sodium thiosulphate. A high amount of nonionic surface active agents in a conventional iodophorous preparation has, however, strongly defatting properties on the skin. Free, elementary iodine is etching the skin, as well.

It is known through French Patent Specification No. 2.029.396 (69.01620) to prepare a iodophorous preparation to be used in disinfecting dairies, breweries, and wine industries whereby an alkylphenoxypoly(ethyleneoxy)ethanol is absorbed on urea, and sulfamic acid. Such a dry product containing 0.25% free iodine is diluted 100 times with water prior to use i.e. to a content of 0.0025% free iodine. Such a solution will, however, not give a sufficient bactericidal effect in disinfecting teats on udders.

DISCLOSURE OF THE PRESENT INVENTION

It has now surprisingly been shown that it is possible to obtain over the prior art an improved udder disinfecting preparation according to the present invention, which preparation is characterized in that it in a ready-to-use form contains an alkylphenoxypoly(ethyleneoxy)-ethanol-iodine complex or a polyvinylpyrrolidone iodine complex in an amount corresponding to at least 0.01% by weight of free iodine, at least 0.04% preferably 0.08% and not more than 2.5%, by weight of a nonionic surface active agent, 5–10% by weight of urea, an organic and/or inorganic acid to pH 1–5, preferably pH 1–3, and water and/or another solvent to 100% by weight.

According to a preferred embodiment the agent moreover contains an alkoxylated glucose derivative in an amount of up to 4% by weight in a ready-to-use solution, preferably 2.5 to 3.5% by weight. According to one preferred embodiment pH is preferably 2.0 to 2.5 acidity may be controlled by employing phosphoric acid, citric acid or hydrochloric acid.

The alkoxylated glucose derivative is according to a preferred embodiment a propoxylated (10 to 20 moles) methyl glucoside.

Foam reducing agents in the form of a nonionic surface active agent can be added, as well.

Iodophorous disinfecting preparations can in normal cases have an iodine concentration in the range of 0.4 to 1.0% in a ready-to-use solution. In tests carried out using a concentration of 2% of iodine no cutaneous toxicity has been observed.

Most iodophors have a content of nonionic surface active agents of 5 to 25%. If iodine and surface active agent act upon each other in any of these products the reaction velocity is dependent on the concentration of the surface active agent and consequently the manufacturer has to keep the concentration of surface active agent as low as possible to obtain a good stability at the same time as the iodine is solubilized. Such products can be used as disinfectants but their effects as detergents will be low. As the problem of stability has been dissolved it is in this special case possible to produce disinfectants having as high detergent activities as 20 to 25%.

An organic solvent as an alcohol can be present to control the viscosity and to give the product anti-freezing properties in countries where low temperatures are present from time to time.

If higher viscosities are preferred viscosity increasing agents known to the one skilled in the art can be added.

The term alkylphenoxypoly(ethyleneoxy)ethanol is understood to mean compounds of the formula

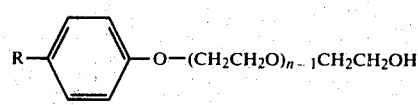

wherein R is an alkyl group preferably having 8 to 10 carbon atoms, especially having 9 carbon atoms. When the alkylphenoxypoly(ethyleneoxy)ethanol is part of a complex with iodine n is an integer 8 to 12, preferably 8–10 and more preferably 9, whereby the ethyleneoxide amount is 60 to 70%, and when the alkylphenoxypoly(ethyleneoxy)ethanol is a nonionic surface active agent in order to obtain a phase stabilizing effect at the dilution of a concentrate to a ready-to-use solution, n is an integer 15 to 40, preferably 20 to 40 and more preferably 30, whereby the ethyleneoxide amount is 75 to 90%. An alkylphenoxypoly(ethyleneoxy)ethanol consisting of nonylphenoxy(ethyleneoxy)ethanol having 23% ethyleneoxide content can be used as a foam reducer.

The amount of iodine in the iodine complex is about 20% (titratable amount).

The amount of iodine in a ready-to-use solution should from a milk contamination point of view not exceed about 0.5% by weight (titratable amount). In the present invention the concentration used is preferably 0.1 to 0.4%, normally 0.25%, of iodine.

From a distributional point of view it is often desired to utilize a concentrate of the iodophorous disinfectant, whereby the concentration of active agent present is up to 5 times as high.

The alkoxylated glucose derivative according to the preferred embodiment is present in a concentrated solution in an amount of up to 15% by weight.

The present invention will in the following be described more in detail with reference to the Examples below.

BEST MODE OF CARRYING OUT THE INVENTION

Example 1

|  | % by weight |
|---|---|
| Antarox VRO 2O (Gaf Corp USA), [nonyl-phenoxypoly(ethyleneoxy)ethanol-iodine complex] 20% free iodine | 3.75 |
| Gaf CO-880 (Gaf Corp USA) [nonylphenoxy-poly(ethyleneoxy)ethanol] | 3.15 |
| Glucam P-10 (Amerchol. USA) [propoxylated methylglucoside] | 4.5 |
| Urea | 24.0 |
| Phosphoric acid | 2.0 |
| Water | 62.60 |

|  | % by weight |
|---|---|
|  | 100.00 |

The solution prepared is diluted with 2 parts of water prior to teat dipping.

Example 2

|  | % by weight |
|---|---|
| Antarox VRO-20 (Gaf Corp. USA) | 3.75 |
| Gaf CO-880 (Gaf Corp. USA) | 3.15 |
| Urea | 24.00 |
| Phosphoric acid (87%) | 2.0 |
| Water | 67.10 |
|  | 100.00 |

The solution prepared is diluted with 2 parts of water prior to teat dipping.

Example 3

| | |
|---|---|
| Betadine ® (Gaf Corp. USA) [PVP-iodine, 10% I] | 7.50 g |
| Urea | 24.00 g |
| Phosphoric acid (87%) to pH 2.5 | |
| Water | to 100.00 g |

The solution prepared is diluted with 2 parts of water prior to teat dipping.

The iodophor according to Example 1 above was compared with a iodophorous udder disinfectant comprising a lanolineiodine complex (Ewodip ®) with regard to bactericidal effect. The ready-to-use solution of Example 1 thereby contained 0.25% by weight of iodine and the agent compared with contained 0.4% by weight of iodine.

The results are shown in the table below where the number of viable microorganisms after 15, 30, and 60 min. have been given.

TABLE 1

| Composition | Amount in % | Microorganism tested | Number, after min | | | |
|---|---|---|---|---|---|---|
| | | | 0 | 15 | 30 | 60 |
| Acc to Ex 1 | 0.25 | Staph aureus | $6 \times 10^7$ | $6.5 \times 10^5$ | $1.5 \times 10^3$ | <1 |
| " | " | Strep uberis | $8.5 \times 10^6$ | $3 \times 10^4$ | $2.5 \times 10^4$ | <1 |
| " | " | Strep dysgalactiae | $3.5 \times 10^7$ | $2 \times 10^3$ | <1 | <1 |
| " | " | Ps aeruginosa | $2.5 \times 10^8$ | $3 \times 10^3$ | <1 | <1 |
| " | " | Strep agalactiae | $2 \times 10^7$ | $3 \times 10^3$ | $\leq 50$ | <1 |
| " | " | E coli | $9 \times 10^7$ | $7.5 \times 10^4$ | $\leq 50$ | $\leq 50$ |
| " | " | Ser marcescens | $5 \times 10^9$ | — | $3 \times 10^3$ | $\leq 50$ |
| " | " | Strep faecalis | $10^9$ | — | $2 \times 10^6$ | $3 \times 10^6$ |
| " | 0.01 | Strep agalactiae | $2.5 \times 10^7$ | — | — | $\leq 50$ |
| " | 0.05 | Strep agalactiae | $2.5 \times 10^7$ | — | — | <1 |
| Ewodip ® | 0.4 | Staph aureus | $6 \times 10^7$ | $2 \times 10^4$ | $1.5 \times 10^4$ | $\leq 50$ |
| " | " | Strep uberis | $8.5 \times 10^6$ | $2.5 \times 10^4$ | 750 | <1 |
| " | " | Strep dysgalactiae | $3.5 \times 10^7$ | $2 \times 10^3$ | 300 | <1 |
| " | " | Ps aeruginosa | $2.5 \times 10^8$ | 700 | $\leq 50$ | <1 |
| " | " | Strep. agalactiae | $2 \times 10^7$ | $4 \times 10^4$ | 50 | $\leq 50$ |
| " | " | E coli | $9 \times 10^7$ | $2 \times 10^4$ | 100 | $\leq 50$ |
| " | " | Ser marcescens | $5 \times 10^9$ | — | $4 \times 10^6$ | $4 \times 10^6$ |
| " | " | Strep faecalis | $10^9$ | — | $2 \times 10^7$ | $2 \times 10^6$ |

As evident from the above the composition according to the present invention has the same or better bactericidal effect than the preparation compared with in spite of the fact that it has a lower iodine concentration.

Compositions according to the present invention, Ex. 1 and Ex. 2, have been tested with regard to skin emollient effect on teats of milking cows compared with above mentioned lanoline-iodine complex. The compositions have thereby been tested in 26 animal stocks comprising totally about 500 animals. The compositions according to the invention have thereby been regarded to be the better than the preparation compared with in 15 stocks, in 7 stocks they have been regarded equally and only in 4 stocks they have been regarded to give a somewhat less skin emollient effect than the preparation compared with. $\chi^2$-test (with Yate's correction) gives the following result.

|  | Superior to | Inferior to |
|---|---|---|
| Found | 15 | 4 |
| Expected | 9.5 | 9.5 |
| $\chi^2 = 5.3$; $0.025 < P < 0.05$ | | |

The composition according to Ex. 1 which was tested in 10 stocks was only regarded to give a worse effect in 1 stock, equal effect in 5 stocks and better effect in 4 stocks than the preparation compared with.

Thus, 22 out of 26 farmers (85%) considered the present compositions to be better than or equal to the preparation compared with.

The compositions of the invention may be used at least once daily during lactation and for the period of at least 2 weeks prior to calving. The teats may be dipped and covered with 1 to 2 mls of solution on each dipping occasion.

Compositions according to the present invention were compared with other iodophorous disinfectants present on the market with regard to bactericidal effect. The results obtained are given in table 2 below.

TABLE 2

| Composition | Amount of I in % | Test organism | Number of viable microorganisms 30 min. | 60 min. |
|---|---|---|---|---|
| Acc. to Ex 1 | 0.25 | Staph. aureus | +++ | − |
|  |  | Str. uberis | +++ | − |
|  |  | Str. dysgalactiae | − | − |
|  |  | Str. agalactiae | + | − |
|  |  | E. coli | + | + |
|  |  | Ps. aeruginosa | − | − |
| Ewodip® | 0.4 | Staph. aureus | +++ | + |
|  |  | Str. uberis | ++ | − |
|  |  | Str. dysgalactiae | ++ | − |

TABLE 2-continued

| Composition | Amount of I in % | Test organism | Number of viable microorganisms 30 min. | 60 min. |
|---|---|---|---|---|
|  |  | Str. agalactiae | + | + |
|  |  | E. coli | + | + |
|  |  | Ps. aeruginosa | + | − |
| Dipal® | 0.4 | Staph. aureus | +++ | + |
|  |  | Str. uberis | +++ | + |
|  |  | Str. dysgalactiae | ++ | − |
|  |  | Str. agalactiae | +++ | − |
|  |  | E. coli | +++ | + |
|  |  | Ps. aeruginosa | +++ | − |
| Iobac | 0.53 | Staph. aureus | +++ | +++ |
|  |  | Str. uberis | +++ | +++ |
|  |  | Str. dysgalactiae | + | + |
|  |  | Str. agalactiae | +++ | +++ |
|  |  | E. coli | + | ++ |
|  |  | Ps. aeruginosa | ++ | + |
| Acc. to Ex 1 | 0.25 | Staph. aureus | + | + |
|  |  | Str. uberis | − | − |
|  |  | Str. dysgalactiae | + | + |
|  |  | Ps. aeruginosa | + | + |
| Acc. to Ex 2 | 0.25 | Staph. aureus | + | − |
|  |  | Str. uberis | + | + |
|  |  | Str. dysgalactiae | + | − |
|  |  | Ps. aeruginosa | ++ | − |
| I-2 (8% glycerine) | 0.4 | Staph. aureus | +++ | + |
|  |  | Str. uberis | + | − |
|  |  | Str. dysgalactiae | +++ | + |
|  |  | Ps. aeruginosa | +++ | + |

− = <1 viable microorganisms
+ = 1–100 viable microorganisms
++ = 100–1000 viable microorganisms
+++ = >1000 viable microorganisms A composition according to Ex. 1 was tested with regard to bactericidal effect and compared with two preparations according to French Pat. Spec. No. 2.029.396 named FP I and FP II, respectively. FP I contained 7.87 g of urea, 2.00 g of 100% phosphoric acid, 0.13 g of Antarox VRO 20, and 990 g of water (iodine concentration 0.0025%). FP II contained 9.87 g of urea, 0.13 g of Antarox VRO 20, and 990.0 g of water (iodine concentration 0.0025%). The results obtained are given in Table 3 below.

TABLE 3

| Composition | Amount of I in % | Test organism | Number of viable microorganisms 0 min | 15 min | 30 min | 60 min |
|---|---|---|---|---|---|---|
| Acc. to Ex 1 | 0.25 | Staph. aureus | $1.5 \times 10^7$ | $1.5 \times 10^3$ | ≦50 | <1 |
|  |  | Str. uberis | $8.5 \times 10^5$ | 100 | <1 | <1 |
|  |  | Str. dysgalactiae | $3 \times 10^7$ | $2.5 \times 10^4$ | <1 | <1 |
|  |  | Ps. aeruginosa | $2.5 \times 10^7$ | $3.5 \times 10^3$ | <1 | <1 |
| FP I | 0.0025 | Staph. aureus | $1.5 \times 10^7$ | $7 \times 10^4$ | $2 \times 10^3$ | 150 |
|  |  | Str. uberis | $8.5 \times 10^5$ | $10^3$ | <1 | <1 |
|  |  | Str. dysgalactiae | $3 \times 10^7$ | $3 \times 10^5$ | $1.5 \times 10^4$ | ≦50 |
|  |  | Ps. aeruginosa | $2.5 \times 10^7$ | $2 \times 10^5$ | 150 | $7 \times 10^3$ |
| FP II | 0.0025 | Staph. aureus | $1.5 \times 10^7$ | $3 \times 10^5$ | $2 \times 10^5$ | $2 \times 10^5$ |
|  |  | Str. uberis | $8.5 \times 10^5$ | $7 \times 10^4$ | $6 \times 10^4$ | $2 \times 10^4$ |
|  |  | Str. dysgalactiae | $3 \times 10^7$ | $4.5 \times 10^5$ | $10^6$ | $3 \times 10^5$ |
|  |  | Ps. aeruginosa | $2.5 \times 10^7$ | $7.5 \times 10^5$ | $1.5 \times 10^6$ | $4.5 \times 10^5$ |

We claim:

1. An iodophorous udder disinfectant comprising an iodophor in the form of an alkylphenoxypoly(ethyleneoxy) ethanol-iodine complex or a polyvinylpyrrolidone-iodine complex, characterized in that in use dilution the disinfectant contains the iodophor complex in an amount sufficient to provide at least 0.01% by weight free iodine, 5 to 10% by weight urea, an acid in an amount sufficient to provide a pH between 1 and 5 and a solvent sufficient to make 100% by weight.

2. An udder disinfectant according to claim 1, wherein the amount of iodophor complex is sufficient to provide from 0.1% to 0.4% free iodine.

3. An udder disinfectant according to claim 1, wherein the amount of acid is sufficient to provide a pH between 1 and 3.

4. A composition according to claim 1, wherein the amount of acid is sufficient to provide a pH between 2 and 2.5.

5. An udder disinfectant according to claim 1, wherein said solvent is water.

6. An udder disinfectant according to one of claims 1, 2, 3, 4 or 5, characterized in that it further contains an alkoxylated glucose derivative in an amount of up to 4% by weight.

7. An udder disinfectant according to claim 6, wherein the alkoxylated glucose derivative is present in an amount between 2.5% and 3.5% by weight.

8. An udder disinfectant according to claim 1, characterized in that the iodine complex is nonylphenoxy(ethyleneoxy)$_{m-1}$ethanol-iodine complex, wherein m is an integer between 8 and 10, which complex is combined with a nonionic surface active agent in an amount of at least 0.08% by weight.

9. An udder disinfectant according to claim 8, characterized in that the nonionic surface active agent is nonylphenoxy(ethyleneoxy)$_{n-1}$ethanol, wherein n is an integer between 20 and 40.

10. An udder disinfectant according to claim 1, characterized in that the acid is at least one acid selected from the group consisting of phosphorous acid, citric acid and hydrochloric acid.

11. An udder disinfectant according to claim 8, characterized in that the nonionic surface acting agent is present in an amount which does not exceed 2.5% by weight.

12. An iodophorous udder disinfectant in concentrated form for preparation of the iodophorous udder disinfectant according to one of claims 1, 2, 3, 4 or 5, characterized in that the concentration of active ingredients present in the concentration is up to five times as high as the concentration in a ready-to-use solution.

13. A method of disinfecting the udders of milkcows in order to improve milk production using an iodophor in the form of an alkylphenoxypoly(ethyleneoxy)-ethanol-iodine complex or a polyvinylpyrrolidone-iodine complex characterized in that the teats of the udders are treated with a solution in accordance with one of claims 1 through 5 or 8 through 11.

14. A method according to claim 13 wherein the teats are treated by being dipped in said udder disinfectant at least once daily during the lactation period and for at least two weeks prior to calving.

15. A method according to claim 13 wherein the teats are dipped and covered with 1 to 2 milliliters of the udder disinfectant at each dipping.

16. A method according to claim 13 characterized in that said solution further contains a alkoxylated glucose derivative in an amount of up to 4% by weight.

17. A method according to claim 16 wherein the alkoxylated glucose derivative is present in an amount between 2.5% and 3.5% by weight.

* * * * *